United States Patent
Vogt et al.

(10) Patent No.: US 7,345,024 B2
(45) Date of Patent: Mar. 18, 2008

(54) PHARMACEUTICAL PREPARATION, METHOD FOR ITS PRODUCTION AS WELL AS ITS USE

(75) Inventors: Sebastian Vogt, Jena (DE); Matthias Schnabelrauch, Jena (DE); Klaus-Dieter Kühn, Marburg (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 28 days.

(21) Appl. No.: 10/600,556

(22) Filed: Jun. 20, 2003

(65) Prior Publication Data

US 2004/0067253 A1    Apr. 8, 2004

(30) Foreign Application Priority Data

Jun. 21, 2002    (DE) .................. 102 27 938

(51) Int. Cl.
 *A61K 31/65* (2006.01)
 *A61K 31/70* (2006.01)
(52) U.S. Cl. ............... 514/35; 514/36; 514/37; 514/38; 514/39; 514/40; 514/152; 514/154
(58) Field of Classification Search ............ 514/35, 514/36, 37, 38, 39, 40, 152, 154; 424/422, 424/464, 468, 489
See application file for complete search history.

(56) References Cited

U.S. PATENT DOCUMENTS

| | | | |
|---|---|---|---|
| 3,091,572 A | 5/1963 | Luedemann et al. | |
| 3,536,759 A | 10/1970 | Jurando et al. | 260/559 |
| 4,291,013 A | 9/1981 | Wahlig et al. | 424/16 |
| 4,617,293 A | 10/1986 | Wahlig et al. | 514/41 |
| 5,459,135 A | 10/1995 | Golub et al. | 514/152 |

FOREIGN PATENT DOCUMENTS

| | | |
|---|---|---|
| DE | 25 17 600 A1 | 12/1975 |
| DE | 32 48 328 A1 | 6/1984 |
| DE | 697 07 927 T2 | 4/2002 |
| EP | 0 420 600 A2 | 4/1991 |
| ES | 354173 | 5/1968 |
| GB | 2 209 938 A | 6/1989 |

OTHER PUBLICATIONS

Renard, G. et al., "Efficacy and safety of a combination of indomethacin and gentamicin after cataract surgery", J. Fr. Ophthalmol., 1996, vol. 19, No. 11, pp. 689-695.
Baeyens, V. et al., "Optimized release of dexamthasone and gentamicin from a soluble ocular insert for the treatment of external ophthalmic infections", J. of Controlled Release, 1998, vol. 52, pp. 215-220.
Van Endt, J.J. et al., "A comparison of two ophthamlmic steroid antibiotic combinations after cataract surgery", European J. of Ophthalmology, 1997, vol. 7, No. 2, pp. 144-148.
European Search Report for EP 03 01 1966, dated Jul. 29, 2003.
G. Renard, et al.; "Comparative study of a collagen corneal shield and a subconjuctival injection at the end of cataract surgery", Journal of Cataract Refract. Surg. 1988, vol. 14, pp. 492-495.

*Primary Examiner*—Elli Peselev
(74) *Attorney, Agent, or Firm*—Norris, McLaughlin & Marcus PA

(57) ABSTRACT

The invention relates to hardly soluble antiphlogistic salts and antiphlogistic-antibiotic pharmaceutical preparations and their use. The hardly water soluble antiphlogistic antibiotics salts have as their cationic component one of the antibiotics gentamicin, clindamycin, neomycin, streptomycin, tetracycline, doxicyline, oxytetracycline and rolitetracycline and as their anionic component one of the antiphlogistics ibuprofen, naproxen, indomethacin, dexamethasone-21-phosphate, dexamethasone-21-sulfate, triamcinolone-21-phosphate and triamcinolone-21-sulfate. The antiphlogistic antibiotics salts are used in pharmaceutical preparations as controlled-release antibiotic/antibiotics drugs. The invention describes antiphlogistic-antibiotic pharmaceutical preparations for which mixtures in the solid state of aggregation are used, which are composed of an easily water soluble salt of gentamicin, clindamycin, neomycin, streptomycin, tetracycline, doxicycline, oxytetracycline and/or rolitetracycline and at least one easily water soluble salt of ibuprofen, naproxen, indomethacin, dexamethasone-21-phosphate, dexamethasone-21-sulfate, triamcinolone-21-phosphate and/or triamcinolone-21-sulfate and at least one inorganic and/or organic pharmaceutical adjuvant and which are used as permanent or temporary implants in the form of tablets and/or molded bodies.

17 Claims, No Drawings

PHARMACEUTICAL PREPARATION, METHOD FOR ITS PRODUCTION AS WELL AS ITS USE

The present invention relates to pharmaceutical preparations, their production as well as their use in human and veterinary medicine for the treatment and prevention of local bacterial infections.

The treatment of local microbial infections of soft and hard tissues in human and veterinary medicine requires high local concentrations of antibiotics in the infected tissue area. It has been known for quite some time that the systemic application of antibiotics is associated with a series of problems. The systemic application often requires the use of very high doses of antibiotics in order to achieve anti-microbially effective antibiotics concentrations in the infected tissue. Thus, particularly with the use of aminoglycoside antibiotics, severe damage to the organism can occur due to their nephro- and oto-toxicity. It therefore seems reasonable to use antibiotics in topical release systems, or transfer them into suitable controlled-release preparations. It is furthermore generally known that especially local microbial infection processes are associated with distinct inflammation processes of the infected tissue, which can lead to additional damage of the infected organism. It is therefore beneficial to take action with antibiotics for local microbial infections as well as for microbial pathogens and simultaneously treat the inflammatory processes.

Controlled-release preparations for the delayed release of antibiotic active ingredients used in the treatment of local infections are the objects of a variety of publications and patents. Apart from physical retarding systems where the retarding effect is essentially based on adsorption effects and diffusion processes, we also know of some retarding systems on the basis of slightly soluble antibiotics salts and antibiotics complexes. Until now hardly soluble salts of the aminoglycoside antibiotics, the tetracycline antibiotics and the lincosamide antibiotics met with relatively little interest in the production of controlled-release preparations. The formation of hardly soluble salts or complexes of the antibiotics of the tetracycline type has been common knowledge for decades. For example the use of tetracycline sulfamates was suggested for antibiotic therapy purposes (A. Jurado Soler, J. M. Puigmarti Codina; Antibiotic tetracycline sulfamate and its derivatives, Oct. 27, 1970, U.S. Pat. No. 3,536,759; Anonymous: Antibiotic tetracycline alkylsulfamates, Oct. 16, 1969, ES 354 173; C. Ciuro, A. Jurado: Stability of a tetracycline derivative. Afinidad 28 (292) 1971, 1333-5). Among the aminoglycoside antibiotics we also basically know a series of hardly soluble salts. For gentamicin, for example, the presentation of hardly soluble salts based on higher fatty acids, arylalkyl carboxylic acids, alkyl sulfates and alkyl sulfonates has been described (G. M. Luedemann, M. J. Weinstein: Gentamycin and method of production, Jul. 16, 1962, U.S. Pat. No. 3,091,572). Examples for this are gentamicin salts of the lauric acid, stearic acid, palmitic acid, oleic acid, phenyl butyric acid, naphthalene-1-carboxylic acid, lauric sulfuric acid and dodecyl benzene sulfonic acid. These salts frequently proved to be not beneficial because they represent wax-like, hydrophobic substances that prevent galenical use. Nevertheless, fatty acid salts were synthesized from gentamicin and from etamycin from the free base and/or their salts in water at 50-80° C. (H. Voege, P. Stadler, H. J. Zeiler, S. Samaan, K. G. Metzger: Sparingly-soluble salts of aminoglycosides and formations containing them with inhibited substance-release, Dec. 28, 1982, DE 32 48 328). These antibiotics fatty acid salts are supposed to be suited as injection preparations. The production of gentamicin dodecyl sulfate and its use in ointments and cremes has also been described (A. Jurado Soler, J. Puigmarti Codina, J. A. Ortiz Hernandez: Neue Gentamicinderivate, Verfahren zur Herstellung derselben und diese enthaltende pharmazeutische Mittel (new gentamicin derivatives, method for production of the same, and pharmaceutical substances containing them), Apr. 21, 1975, DE 25 17 600). Among the lincosamide antibiotics as well hardly soluble salts, such as e.g. glindamycin palmitate, are known (M. Cimbollek, B. Nies, R. Wenz, J, Kreuter: Antibiotic-impregnated heart valve sewing rings for treatment and prophylaxis of bacterial endocarditis. Antimicrob. Agents Chemother. 40(6) (1996) 1432-1437). A more recent development are hardly soluble aminoglycoside flavonoid phosphates (H. Wahlig, E. Dingeldein, R. Kirchlechner, D. Orth, W. Rogalski: Flavonoid phosphate salts of aminoglycoside antibiotics, Oct. 13, 1986, U.S. Pat. No. 4,617,293). It describes the salts of the phosphoric acid semi-esters of derivatives of the hydroxy flavanes, hydroxy flavenes, hydroxy flavanones, hydroxy flavones and hydroxy flavylium. Particularly preferred are the derivatives of the flavanones and the flavones. These hardly soluble salts are supposed to be used as controlled-release preparations. These salts are for example introduced into collagen fleece (H. Wahlig, E. Dingeldein, D. Braun: Medicinally useful, shaped mass of collagen resorbable in the body, Sep. 22, 1981, U.S. Pat. No. 4,291,013).

So far no publications about antibiotic-antiphlogistic preparations are known that are based on hardly water soluble salts composed of an antiphlogistic from the group of the steroid antiphlogistics and the non-steroid arylalkyl carboxylic acids and from at least one of the antibiotics gentamicin, clindamycin, neomycin, streptomycin, tetracycline, doxicycline, oxytetracycline and rolitetracycline.

The present invention is based on the task of developing a pharmaceutical preparation as an antiphlogistics-antibiotics combination with retarding active ingredient release as a controlled-release antibiotics preparation for human and veterinary medicine, for the treatment of local microbial infections in bone and in soft tissues.

The task is resolved pursuant to the present invention with the features of the broad and preferred descriptions hereinbelow.

Gentamicin, clindamycin, neomycin, streptomycin, tetracycline, doxicycline, oxytetracycline and rolitetracycline are frequently employed cationic antibiotics, whose amino groups are protonized in the salt form and which form easily water soluble salts with conventional anions, such as e.g. sulfate anions and chloride anions. The alkali salt forms of the antiphlogistics ibuprofen, naproxen, indomethacin, dexamethasone-21-phosphate, dexamethasone-21-sulfate, triamcinolone-21-phosphate and triamcinolone-21-sulfate are also easily water-soluble.

This combination exhibits a controlled release of antibiotics and also of antiphlogistics in an aqueous environment over a period of several days. The mechanism of the delayed active ingredient release is essentially independent from carrier materials and is not based on adsorption effects on the surfaces of carrier materials. The antiphlogistics/antibiotics combination can be processed into implants both with resorbable and also with non-resorbable adjuvants while maintaining the retarding active ingredient release effect. Additionally, the type of the active ingredient combination can be applied not only to a special antibiotic, but it is rather suited for a series of antibiotics with similar structures.

The invention is based on the surprising finding that salts whose cationic component contains at least one representative from the antibiotics gentamicin, clindamycin, neomycin, streptomycin, tetracycline, doxicyline, oxytetracycline and rolitetracycline and whose anionic component contains at least one representative from the antiphlogistics ibuprofen, naproxen, indomethacin, dexamethasone-21-phosphate, dexamethasone-21-sulfate, triamcinolone-21-phosphate and triamcinolone-21-sulfate are hardly water-soluble.

These salts can be formed from the water soluble salts of the antibiotics gentamicin, clindamycin, neomycin, streptomycin, tetracycline, doxicyline, oxytetracycline and rolitetracycline and the water soluble alkali salts of the antiphlogistics ibuprofen, naproxen, indomethacin, dexamethasone-21-phosphate, dexamethasone-21-sulfate, triamcinolone-21-phosphate and triamcinolone-21-sulfate through reciprocal salt exchange. The production can take place by mixing the antibiotics salts, which have been dissolved in water, with the antiphlogistics salts, which have also been dissolved in water, wherein the hardly water soluble antiphlogistic antibiotics salts precipitate as solid matter or oils.

It is beneficial that the salts gentamicin-ibuprofen, gentamicin-naproxen, gentamicin-indomethacin, gentamicin-dexamethasone-21-phosphate, gentamicin-triamcinolone-21-phosphate, tetracycline-indomethacin, tetracycline-indomethacin, neomycin-indomethacin, clindamycin-indomethacin, streptomycin-naproxen, tetracycline-naproxen, clindamycin-naproxen, streptomycin-ibuprofen are preferred.

Furthermore it is useful that the antiphlogistic antibiotics salts are introduced in molded bodies, tablets, powders, granules, fibers, knitted fabrics and fleece, which pursuant to the invention are used as permanent or temporary implants. This means that the antiphlogistic antibiotics salts are integrated into tablets, powders, granules, fibers, knitted fabrics and fleece as pharmaceutically active combinations of active ingredients.

It is useful that the salts are part of coatings that are applied onto molded bodies, powders, granules, fibers, knitted fabrics and fleece, which pursuant to the invention are used as permanent or temporary implants. These coatings can consist of the antiphlogistic antibiotics salts as such or of combinations with a polymer layer-forming agent.

The invention is based on the additional surprising finding that mixtures in the solid state of aggregation, which are composed of an easily water soluble salt of gentamicin, clindamycin, neomycin, streptomycin, tetracycline, doxicycline, oxytetracycline and/or rolitetracycline and at least one easily water soluble salt of ibuprofen, naproxen, indomethacin, dexamethasone-21-phosphate, dexamethasone-21-sulfate, triamcinolone-21-phosphate and/or triamcinolone-21-sulfate and at least one inorganic and/or organic pharmaceutical adjuvant, form the controlled-release antibiotics preparations. These combinations can be pressed for example into tablets or molded bodies. It was surprisingly learned that these tables and molded bodies exhibit a retarding active ingredient release effect in an aqueous environment. This finding can be attributed to the fact that after introducing the tablets and molded bodies into an aqueous environment the effect of the water causes hardly water soluble salts to develop. This means that the cost-intensive synthesis of the antiphlogistic antibiotics salts can be foregone by employing the invented mixtures composed of at least one easily water soluble salt of gentamicin, clindamycin, neomycin, streptomycin, tetracycline, doxicycline, oxytetracycline and/or rolitetracycline and at least one easily water soluble salt of ibuprofen, naproxen, indomethacin, dexamethasone-21-phosphate, dexamethasone-21-sulfate, triamcinolone-21-phosphate and/or triamcinolone-21-sulfate and at least one inorganic and/or organic pharmaceutical adjuvant for the production of tablets and molded bodies. This surprising finding is essential for the extremely inexpensive production of tablets and molded bodies.

The object of the present invention shall be explained in the following in more detail based on the examples 1 through 5, however without limit the invention.

EXAMPLE 1

Production of Gentamicin Dexamethasone Phosphate 150 mg gentamicin sulfate (AK 628) are dissolved in 1 ml dist. water and separately from that 120 mg dexamethasone-21-phosphate sodium salt (Fluka) are also dissolved in 2 ml distilled water. Subsequently, while being stirred, the dexamethasone-21-phosphate-sodium salt solution is added in drops to the gentamicin sulfate solution. The precipitate is flaky and slimy. Dexamethasone-21-phosphate-sodium salt solution continues to be added in drops until no more precipitate develops. The precipitate is rinsed several times with distilled water and subsequently dried to mass consistency.

Yield: 163 mg; Fp~235 (decomposition); IR □ ($cm^{-1}$): 3600-3000 (□ OH); 2943 (□CH); 2871 (□CH); 1716 (□CO); 1664 (Aromat); 1620; 1466; 1394; 1245; 1100; 983; 890; 851; 529.

EXAMPLE 2

A mixture of 1,000.0 mg calcium sulfate dihydrate (Fluka), 250.0 mg poly-L-lactide (M-10,000 g/mol), 49.7 mg gentamicin sulfate (AK 628) and 24.9 mg dexamethasone-21-phosphate sodium salt (Fluka) is ground up. 200 mg of this mixture, respectively, are pressed with a press at a pressure of 5 tons within a period of two minutes into disk-shaped molded bodies with a diameter of 13 mm.

EXAMPLE 3

A mixture of 1,000.0 mg calcium sulfate dihydrate (Fluka), 250.0 mg poly-L-lactide (M-10,000 g/mol), 49.7 mg gentamicin sulfate (AK 628) and 86.8 mg naproxen sodium salt (produced through the neutralization of naproxen (Fluka)) is ground up. 200 mg of this mixture, respectively, are pressed with a press at a pressure of 5 tons within a period of two minutes into disk-shaped molded bodies with a diameter of 13 mm.

EXAMPLE 4

A mixture of 1,000.0 mg calcium sulfate dihydrate (Fluka), 250.0 mg poly-L-lactide (M-10,000 g/mol), 49.7 mg gentamicin sulfate (AK 628) and 78.5 mg ibuprofen sodium salt (produced through the neutralization of ibuprofen (Fluka)) is ground up. 200 mg of this mixture, respectively, are pressed with a press at a pressure of 5 tons within a period of two minutes into disk-shaped molded bodies with a diameter of 13 mm.

EXAMPLE 5

A mixture of 1,000.0 mg calcium sulfate dihydrate (Fluka), 250.0 mg poly-L-lactide (M-10,000 g/mol), 49.7 mg gentamicin sulfate (AK 628) and 130.7 mg indomethacin sodium salt (produced through neutralization (Fluka)) is ground up. 200 mg of this mixture, respectively, are pressed with a press at a pressure of 5 tons within a period of two minutes into disk-shaped molded bodies with a diameter of 13 mm.

Antibiotics Release Experiments

The molded bodies produced in the examples 2-5 were introduced into Sörensen buffer with pH 7.4 and stored in it at 37° C. over a period of two weeks. Sampling took place on a daily basis, wherein the release medium was replaced. The antibiotics value determination was performed with an agar diffusion test while employing *bacillus subtilis* ATCC 6633 as the test germ. The results are depicted in the table.

TABLE

Cumulative gentamicin release (as gentamicin base) from the molded bodies of examples 2-5 in dependency upon the storage time in the Sörensen buffer at 37° C.

Cumulative Release of Gentamicin (as gentamicin base) [mg]

Storage Time [d]

| Examples | 1 | 2 | 3 | 4 | 5 | 6 | 7 | 8 |
|---|---|---|---|---|---|---|---|---|
| 2 | 2.80 | 3.22 | 3.46 | 3.60 | 3.74 | 3.83 | 3.90 | 3.95 |
| 3 | 2.08 | 3.05 | 3.61 | 3.86 | 3.90 | 3.92 | 3.93 | 3.93 |
| 4 | 1.64 | 2.03 | 2.36 | 2.71 | 3.20 | 3.40 | 3.59 | 3.82 |
| 5 | 2.83 | 3.22 | 3.31 | 3.34 | 3.34 | 3.45 | 3.45 | 3.45 |

What is claimed is:

1. Pharmaceutical preparation, comprising at least one antiphlogistic-antibiotic salt whose cationic component contains at least one representative from the antibiotics gentamicin, clindamycin, neomycin, streptomycin, tetracycline, doxicyline, oxytetracycline and rolitetracycline and whose anionic component contains at least one representative from the antiphlogistics ibuprofen, naproxen, indomethacin, dexamethasone-21-phosphate, dexamethasone-21-sulfate, triamcinolone-21-phosphate and triamcinolone-21-sulfate, which pharmaceutical preparation is in the form of at least one member selected from the group consisting of molded bodies, tablets, powders, granules, fibers, knitted fabrics and fleece.

2. Pharmaceutical preparation pursuant to claim 1, comprising at least one antiphlogistic-antibiotic salt of gentamicin-ibuprofen, gentamicin-naproxen, gentamicin-indomethacin, gentamicin-dexamethasone-21-phosphate, gentamicin-triamcinolone-21-phosphate, tetracycline-indomethacin, tetracycline-indomethacin, neomycin-indomethacin, clindamycin-indomethacin, streptomycin-naproxen, tetracycline-naproxen, clindamycin-naproxen, or streptomycin-ibuprofen.

3. Pharmaceutical preparation, comprising at least one antiphlogistic-antibiotic salt whose cationic component contains at least one representative from the antibiotics gentamicin, clindamycin, neomycin, streptomycin, tetracycline, doxicyline, oxytetracycline and rolitetracycline and whose anionic component contains at least one representative from the antiphlogistics ibuprofen, naproxen, indomethacin, dexamethasone-21-phosphate, dexamethasone-21-sulfate, triamcinolone-21-phosphate and triamcinolone-21-sulfate, which pharmaceutical preparation is part of a coating applied onto at least one member selected from the group consisting of molded bodies, powders, granules, fibers, knitted fabrics and fleece.

4. Pharmaceutical preparation, comprising a mixture in a solid state of aggregation, which mixture is composed of at least one easily water soluble salt of at least one of gentamicin, clindamycin, neomycin, streptomycin, tetracycline, doxicycline, oxytetracycline and/or rolitetracycline and at least one easily water soluble salt of at least one of ibuprofen, naproxen, indomethacin, dexamethasone-21-phosphate, dexamethasone-21-sulfate, triamcinolone-21-phosphate and/or triamcinolone-21-sulfate and at least one inorganic and/or organic pharmaceutical adjuvant, and said pharmaceutical preparation has a shape of tablets and/or molded bodies.

5. Method for producing a pharmaceutical preparation pursuant to claim 1, comprising the following steps:
   a) mixing an easily water soluble salt of at least one of gentamicin, clindamycin, neomycin, streptomycin, tetracycline, doxicycline, oxytetracycline and/or rolitetracycline with at least one easily water soluble salt of at least one of ibuprofen, naproxen, indomethacin, dexamethasone-21-phosphate, dexamethasone-21-sulfate, triamcinolone-21-phosphate and/or triamcinolone-21-sulfate, and forming the at least one antiphlogistic-antibiotic salt by reciprocal salt exchange; and
   b) forming the pharmaceutical preparation into the form of at least one member selected from the group consisting of molded bodies, tablets, powders, granules, fibers, knitted fabrics and fleece.

6. Method for producing a pharmaceutical preparation pursuant to claim 4, comprising the following steps:
   a) mixing the at least one easily water soluble salt of at least one of gentamicin, clindamycin, neomycin, streptomycin, tetracycline, doxicycline, oxytetracycline and/or rolitetracycline with the at least one easily water soluble salt of at least one of ibuprofen, naproxen, indomethacin, dexamethasone-21-phosphate, dexamethasone-21-sulfate, triamcinolone-21-phosphate and/or triamcinolone-21-sulfate and the at least one inorganic and/or organic pharmaceutical adjuvant; and
   b) forming the pharmaceutical preparation into the shape of tablets and/or molded bodies.

7. A method of treating a bacterial infection in a patient comprising administering a pharmaceutical preparation pursuant to claim 1 to said patient as a controlled-release antibiotics drug.

8. A permanent or temporary implant comprising a pharmaceutical preparation, comprising at least one antiphlogistic-antibiotic salt whose cationic component contains at least one representative from the antibiotics gentamicin, clindamycin, neomycin, streptomycin, tetracycline, doxicyline, oxytetracycline and rolitetracycline and whose anionic component contains at least one representative from the antiphlogistics ibuprofen, naproxen, indomethacin, dexamethasone-21-phosphate, dexamethasone-21-sulfate, triamcinolone-21-phosphate and triamcinolone-21-sulfate, which pharmaceutical preparation is in the form of at least one member selected from the group consisting of molded bodies, tablets, powders, granules, fibers, knitted fabrics and fleece.

9. A permanent or temporary implant comprising a pharmaceutical preparation, comprising a mixture in a solid state of aggregation, which mixture is composed of at least one easily water soluble salt of at least one of gentamicin, clindamycin, neomycin, streptomycin, tetracycline, doxicycline, oxytetracycline and/or rolitetracycline and at least one easily water soluble salt of at least one of ibuprofen, naproxen, indomethacin, dexamethasone-21-phosphate, dexamethasone-21-sulfate, triamcinolone-21-phosphate and/or triamcinolone-21-sulfate and at least one inorganic and/or organic pharmaceutical adjuvant, and said pharmaceutical preparation has a shape of tablets and/or molded bodies.

10. A method for producing a pharmaceutical preparation according to claim 5, wherein said pharmaceutical preparation is formed into tablet and/or molded body form.

11. A method for producing a pharmaceutical preparation according to claim 6, wherein said pharmaceutical preparation is formed into molded body form.

12. The method according to claim 5, wherein said forming the at least one antiphlogistic-antibiotic salt by reciprocal salt exchange comprises precipitating the antiphlogistic-antibiotic salt.

13. The method according to claim 6, which further comprises precipitating antipholgistic-antibiotics salts by introducing the tablets and/or molded bodies into water.

14. Pharmaceutical preparation pursuant to claim 3, comprising at least one antiphlogistic-antibiotic salt of gentamicin-ibuprofen, gentamicin-naproxen, gentamicin-indomethacin, gentamicin-dexamethasone-21-phosphate, gentamicin-triamcinolone-21-phosphate, tetracycline-indomethacin, tetracycline-indomethacin, neomycin-indomethacin, clindamycin-indomethacin, streptomycin-naproxen, tetracycline-naproxen, clindamycin-naproxen, or streptomycin-ibuprofen.

15. Pharmaceutical preparation pursuant to claim 4, comprising at least one salt of gentamicin-ibuprofen, gentamicin-naproxen, gentamicin-indomethacin, gentamicin-dexamethasone-21-phosphate, gentamicin-triamcinolone-21-phosphate, tetracycline-indomethacin, neomycin-indomethacin, clindamycin-indomethacin, streptomycin-naproxen, tetracycline-naproxen, clindamycin-naproxen, or streptomycin-ibuprofen.

16. Pharmaceutical preparation pursuant to claim 8, comprising at least one antiphlogistic-antibiotic salt of gentamicin-ibuprofen, gentamicin-naproxen, gentamicin-indomethacin, gentamicin-dexamethasone-21-phosphate, gentamicin-triamcinolone-21-phosphate, tetracycline-indomethacin, tetracycline-indomethacin, neomycin-indomethacin, clindamycin-indomethacin, streptomycin-naproxen, tetracycline-naproxen, clindamycin-naproxen, or streptomycin-ibuprofen.

17. The implant pursuant to claim 9, wherein the pharmaceutical preparation comprises at least one salt of gentamicin-ibuprofen, gentamicin-naproxen, gentamicin-indomethacin, gentamicin-dexamethasone-21-phosphate, gentamicin-triamcinolone-21-phosphate, tetracycline-indomethacin, tetracycline-indomethacin, neomycin-indomethacin, clindamycin-indomethacin, streptomycin-naproxen, tetracycline-naproxen, clindamycin-naproxen, or streptomycin-ibuprofen.

* * * * *